US00PP31520P2

(12) United States Plant Patent
Egger

(10) Patent No.: US PP31,520 P2
(45) Date of Patent: Mar. 3, 2020

(54) ***PENSTEMON* PLANT NAMED 'TNPENHPU'**

(50) Latin Name: ***Penstemon* hybrid**
Varietal Denomination: TNPENHPU

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/350,946

(22) Filed: Feb. 4, 2019

(51) Int. Cl.
*A01H 5/02* (2018.01)
*A01H 6/68* (2018.01)

(52) U.S. Cl.
USPC ..... Plt./465
CPC ..... *A01H 6/68* (2018.05)

(58) Field of Classification Search
USPC ..... Plt./465
See application file for complete search history.

*Primary Examiner* — Anne Marie Grunberg
(74) *Attorney, Agent, or Firm* — Klarquist Sparkman, LLP

(57) ABSTRACT

A new and distinct *Penstemon* plant characterized by dense clusters of medium-size, purple flowers with white throats; long bloom time; good rebloom; compact, upright, well-branched habit with multiple crowns from the base; and excellent vigor.

1 Drawing Sheet

Botanical denomination: *Penstemon* hybrid.
Variety designation: 'TNPENHPU'.

BACKGROUND OF THE INVENTION

The present invention relates to a new and distinct *Penstemon* plant given the name 'TNPENHPU'. *Penstemon* is in the family Scrophulariaceae. *Penstemon* 'TNPENHPU' originated from open-pollinated seeds of *Penstemon* '248-2', an unnamed, unpatented, proprietary plant. It was part of a controlled breeding program to create a compact, upright, medium-small-size, reblooming, and hardy series. This seedling was selected for its medium-size purple flowers with white throats; flowers in dense clusters; long bloom time; good rebloom; compact, upright, well-branched habit, with multiple crowns from the base; vigor; and clean, attractive look. It is an ideal plant for a sunny border in full sun.

SUMMARY OF THE INVENTION

The present invention has not been evaluated under all possible environmental conditions. The phenotype may vary with variations in environment without a change in the genotype of the plant.

*Penstemon* 'TNPENHPU' is uniquely distinguished by its:

1. medium-size purple flowers with white throats in dense clusters,
2. long bloom time,
3. good rebloom,
4. compact, upright, well-branched habit with multiple crowns from the base,
5. clean-looking, attractive foliage, and
6. excellent vigor.

Compared to the seed parent, *Penstemon* '248-2', the new plant has a more upright habit rather than floppy habit.

Compared to *Penstemon* 'P007S', an unpatented plant, the new plant is more floriferous and has more crowns.

Compared to *Penstemon* 'Cha Cha Purple' (U.S. Plant Pat. No. 26,698), the new plant has a shorter habit and smaller and narrower leaves.

Trade Designation: HARLEQUIN™ Purple.

The new variety has been reproduced only by asexual propagation (cuttings and micropropagation). Each of the progeny exhibits identical characteristics to the original plant. Asexual propagation by cuttings and micropropagation using terminal and lateral shoots, as done in Canby, Oreg., shows that the foregoing characteristics and distinctions come true to form and are established and transmitted through succeeding propagations.

BRIEF DESCRIPTION OF THE DRAWINGS

FIG. 1 shows a close up of the plant as a 2-year-old in a trial field in full bloom in mid-June in Canby, Oreg.

FIG. 2 shows the plant as a 2-year-old in a trial field in full bloom in mid-June in Canby, Oreg.

DETAILED PLANT DESCRIPTION

The following is a detailed description of the new *Penstemon* plant based on observations of 2-year-old specimens grown outside in a trial field in full sun in Canby, Oreg. in October. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart, 5th* edition, 2007.

Plant:

*Type*.—Herbaceous perennial.
*Form*.—Upright, branching.
*Cold hardiness*.—USDA Zone 6-10.
*Size*.—Grows to 68 cm wide and 54 cm tall.
*Vigor*.—Excellent.
*Stem number*.—About 23 main stems from the crown.
*Stem strength*.—Strong.

*Stem*.—Strongly upright, branched with branches strongly upright, grows to 47 cm long to the main inflorescence and 5 mm wide (at the base), glabrous, internodes grow to 4.5 cm long, Yellow Green 146C, tinted with Grey Brown N199A at base.

*Roots and rooting*.—Fibrous root system, White 155C, roots easily from stem cuttings in 10 to 14 days.

Leaf:

*Type*.—Simple.

*Arrangement*.—Opposite.

*Shape*.—Lanceolate.

*Venation*.—Pinnate, main vein Yellow Green 145B both sides.

*Margins*.—Serrulate.

*Apex*.—Acute.

*Base*.—Sessile.

*Petiole*.—None, sessile.

*Blade size*.—Grows to 6.8 cm long and 1.2 cm wide.

*Surface texture*.—Glabrous on both sides.

*Leaf color*.—Topside Green 137B, bottom side closest to Green 138A.

Inflorescence:

*Type*.—Terminal, many flowered, dense thyrse.

*Number of flowers per inflorescence*.—20 to 45.

*Size of inflorescence*.—Grows to 13 cm long and 6.5 cm wide.

*Peduncle*.—Strong, upright, grows to 1.8 cm long and 2 mm wide, glandular pubescent, closest to Yellow Green 146C.

*Pedicel*.—Medium strength, grows upright to 0.5 cm long and 1 mm wide, glandular pubescent, Yellow Green 146C tinted Greyed Purple 187A where exposed to sunlight.

*Bloom period*.—Mid-May to frost in November in Canby, Oreg. if spent flowers are removed.

Flower bud:

*Size*.—2.2 cm long and 0.8 cm wide.

*Description*.—Closed tubular, bulging, flattened centrically, pubescent.

*Color*.—Topside of bud closest to Purple N79A at tip blending to Purple N79B towards base, tip of base White NN155A usually covered by calyx.

Flower:

*Type*.—Zygomorphic, perfect.

*Shape*.—Tubular, bilabiate.

*Size*.—Grows to 3 cm long and 1.5 cm wide.

*Corolla description*.—Grows to 2.9 cm long and 1.5 cm wide; tube is bulbous in the calyx for 0.4 cm long and 0.4 cm wide, narrowing then widening for 2.5 cm and flaring to 1.5 cm wide, 5 lobes; top 2 lobes 1 cm long and 0.5 cm wide, 3 bottom lobes 1 cm and 6 wide; lobe margins entire, tips obtuse; outside glandular pubescent, inside sparsely pubescent; topside of flower between Purple N79A and Purple N79C at tip blending to Purple N79C at base; inside color Purple N79A on top 2 lobes, 3 bottom lobes have streaks of Purple N79A and White NN155D beginning 0.5 cm below tip of lobes.

*Calyx description*.—8 mm deep and 8 mm wide, 5 lobes cut to the base; lobes lanceolate, 8 mm deep and 0.2 cm wide; margins entire; tip acuminate; base cuneate; outside Yellow Green 145B heavily tinted Greyed Purple 187A in high light; inside Yellow Green 145B; outside pubescent; inside glabrous.

*Pistil description*.—1, 2.1 cm long, ovary 0.3 cm long and 1.5 mm wide, Yellow Green 144C; style 1.6 cm long and less than 1 mm wide, style White NN155C; stigma 0.2 cm flattened, White NN155C.

*Stamen description*.—5, one sterile without an anther, held within the corolla 2.3 cm long; filaments 2.3 cm to 3 cm long and less than 1 mm wide, White NN155C; anthers horseshoe-shaped, 3 mm long and 2 mm wide, Black 202 A; pollen amount low, White NN155C.

*Fragrance*.—None.

*Lastingness*.—A flower lasts 5 to 6 days.

Fruit:

*Type*.—Capsule.

*Fertility*.—Poor.

*Size*.—7 mm deep and 5 mm wide.

*Texture*.—Glabrous.

*Color*.—Brown N199C.

Seed:

*Shape*.—Irregular.

*Size*.—1 mm long.

*Texture*.—Glabrous.

*Color*.—Brown 200A.

Pests and diseases: The new plant is typical to the genus. No problems have been found in Canby, Oreg.

I claim:

1. A new and distinct *Penstemon* plant illustrated as shown and described.

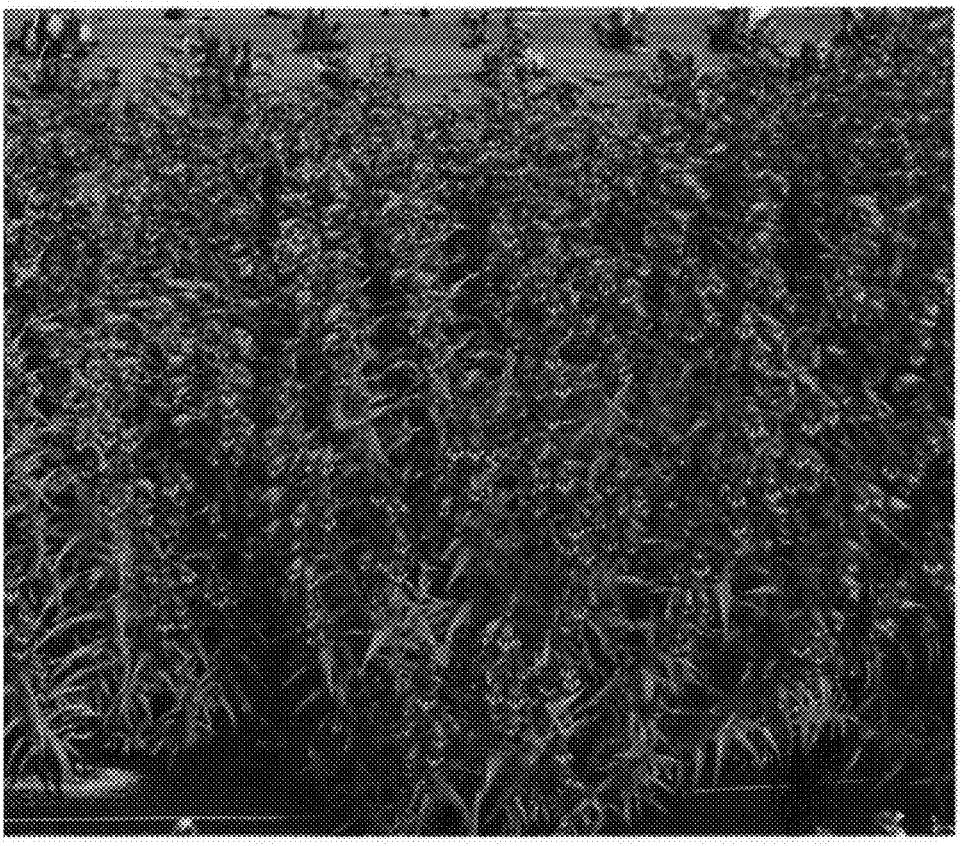
Fig. 1
Fig. 2
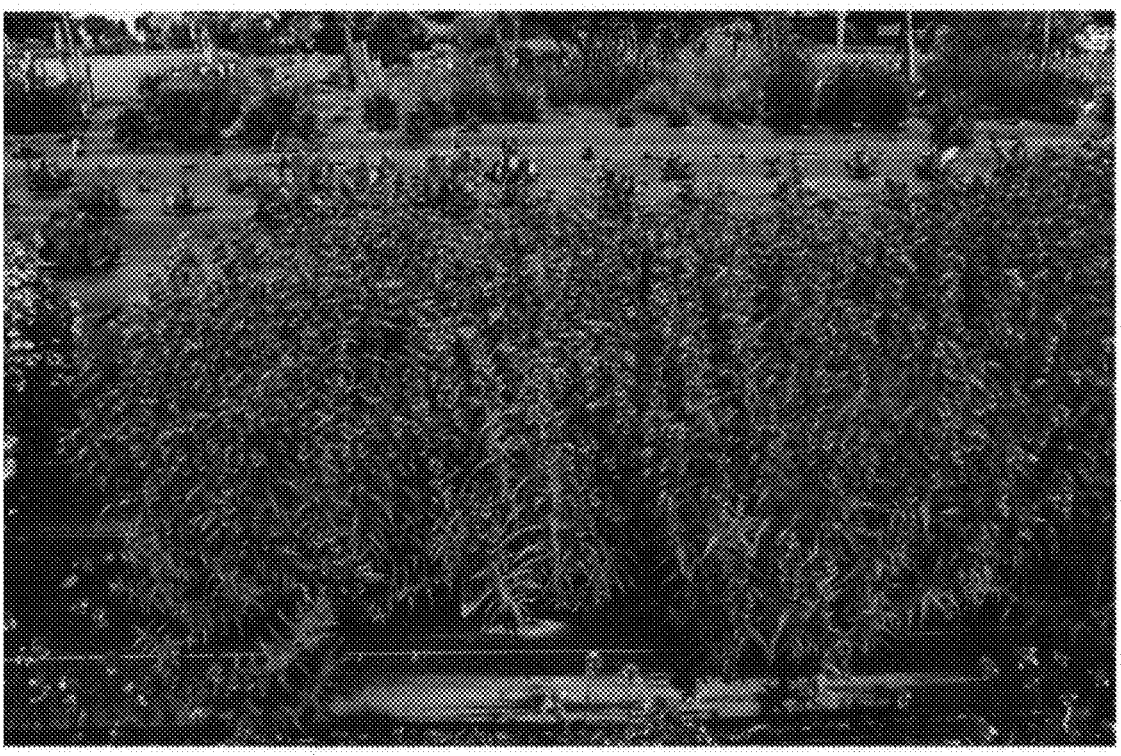

* * * * *